United States Patent
Nieskens et al.

(10) Patent No.: US 10,787,611 B2
(45) Date of Patent: Sep. 29, 2020

(54) PROCESS TO CONVERT SYNTHESIS GAS TO OLEFINS USING A BIFUNCTIONAL CHROMIUM/ZINC OXIDE-SAPO-34 CATALYST

(71) Applicant: Dow Global Technologies LLC, Midland, MI (US)

(72) Inventors: Davy L. S. Nieskens, Terneuzen (NL); Aysegul Ciftci Sandikci, Eindhoven (NL); Peter E. Groenendijk, Ternezeun (NL); Andrzej Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/471,170

(22) PCT Filed: Dec. 21, 2017

(86) PCT No.: PCT/US2017/067822
§ 371 (c)(1),
(2) Date: Jun. 19, 2019

(87) PCT Pub. No.: WO2018/119195
PCT Pub. Date: Jun. 28, 2018

(65) Prior Publication Data
US 2020/0017774 A1 Jan. 16, 2020

Related U.S. Application Data

(60) Provisional application No. 62/438,035, filed on Dec. 22, 2016.

(51) Int. Cl.
*C10G 2/00* (2006.01)
*C07C 1/04* (2006.01)
(Continued)

(52) U.S. Cl.
CPC ............... *C10G 2/33* (2013.01); *B01J 23/06* (2013.01); *B01J 23/26* (2013.01); *B01J 29/85* (2013.01);
(Continued)

(58) Field of Classification Search
None
See application file for complete search history.

(56) References Cited

U.S. PATENT DOCUMENTS

| 8,513,315 B2 | 8/2013 | Kibby |
| 10,329,209 B2 | 6/2019 | Nieskens et al. |
| 2008/0319245 A1 | 12/2008 | Fujimoto et al. |

FOREIGN PATENT DOCUMENTS

| CN | 103071528 A | 5/2013 |
| CN | 103508828 A | 1/2014 |

(Continued)

OTHER PUBLICATIONS

Wu et al., "Methanol conversion on SAPO-34: reaction condition for fixed bed reactor," Appl. Catal. A: Gen. 260, 63-69, 2004.
(Continued)

*Primary Examiner* — Medhanit W Bahta
(74) *Attorney, Agent, or Firm* — Dinsmore & Shohl LLP

(57) ABSTRACT

A process for preparing $C_2$ to $C_3$ olefins includes introducing a feed stream having a volumetric ratio of hydrogen to carbon monoxide from greater than 0.5:1 to less than 5:1 into a reactor, and contacting the feed stream with a bifunctional catalyst. The bifunctional catalyst includes a Cr/Zn oxide methanol synthesis component having a Cr to Zn molar ratio from greater than 1.0:1 to less than 2.15:1, and a SAPO-34 silicoaluminophosphate microporous crystalline material. The reactor operates at a temperature ranging from 350° C. to 450° C., and a pressure ranging from 10 bar (1.0 MPa) to 60 bar (6.0 MPa). The process has a cumulative
(Continued)

productivity of $C_2$ to $C_3$ olefins greater than 15 kg $C_2$ to $C_3$ olefins/kg catalyst.

20 Claims, 1 Drawing Sheet

(51) Int. Cl.
    *B01J 23/06*        (2006.01)
    *B01J 23/26*        (2006.01)
    *B01J 29/85*        (2006.01)
    *B01J 37/18*        (2006.01)
    *C01B 39/54*        (2006.01)

(52) U.S. Cl.
    CPC ............... *B01J 37/18* (2013.01); *C01B 39/54* (2013.01); *C07C 1/043* (2013.01); *C07C 1/0445* (2013.01); *C10G 2/334* (2013.01); *C07C 2523/06* (2013.01); *C07C 2523/26* (2013.01); *C07C 2529/85* (2013.01); *C10G 2300/1022* (2013.01); *C10G 2300/70* (2013.01); *C10G 2400/20* (2013.01)

(56) References Cited

FOREIGN PATENT DOCUMENTS

| | | |
|---|---|---|
| WO | 2010068364 A2 | 6/2010 |
| WO | 2016007607 A1 | 1/2016 |

OTHER PUBLICATIONS

Lok et al., "Silicoalumino-phosphate Molecular Sieves: Another New Class of Microporous Crystalline Inorganic Solids," J. Am. Chem. Soc. 106 (1984) 6092-6093.

Liu et al., "Synthesis of SAPO-34 templated by diethylamine: Crystallization process and Si distribution in the crystals," Microporous and Mesoporous Materials, 114 (2008) 1-3, 416-423.

Ye et al., "Synthesis Optimization of SAPO-34 in the Presence of Mixed Template for MTO Process," Adv. Matl. Research, 132 (2010) 246-256.

Li et. al, "Direct conversion of syngas into hydrocarbons over a core-shell Cr—Zn@SiO2@-SAPO-34 catalyst," Chinese J. Catal. 36 (2015) 1131-1135.

Cheng et al., "Direct and Highly Selective Conversion of Synthesis Gas to Lower Olefins: Design of a Bifunctional Catalyst Combining Methanol Synthesis and Carbon-Carbon Coupling", Angew. Chem. Int. Ed., 2016, 1-5.

Jiao et al., "Selective Conversion of Syngas to Light Olefins", Science, 2016, 351, 1065.

International Search Report and Written Opinion pertaining to PCT/US2017/067822, dated Mar. 27, 2018.

Dawood et al, "Catalyse Bifonctionnelle: Hydrocondensation Du Monoxyde De Carbone Sur Cu/Zn-Mordenite", Nouveau Journal de Chimie, 8 (1984) pp. 601-604.

Simard et al., "ZnO—Cr2O3=ZSM-5 Catalyst with Very Low Zn—Cr Ratio for the Transformation of Synthesis Gas to Hydrocarbons", Applied Catalysis A: General, 125 (1995) pp. 81-98.

Erena et al., "Study of Physical Mixtures of Cr2O3—ZnO and ZSM-5 Catalysts for the Transformation of Syngas into Liquid Hydrocarbons", Ind. Eng. Chem. Res. 37 (1998) pp. 1211-1219.

Examination Report pertaining to corresponding Gulf Cooperation Council Application No. 2017-34430, dated Nov. 12, 2019.

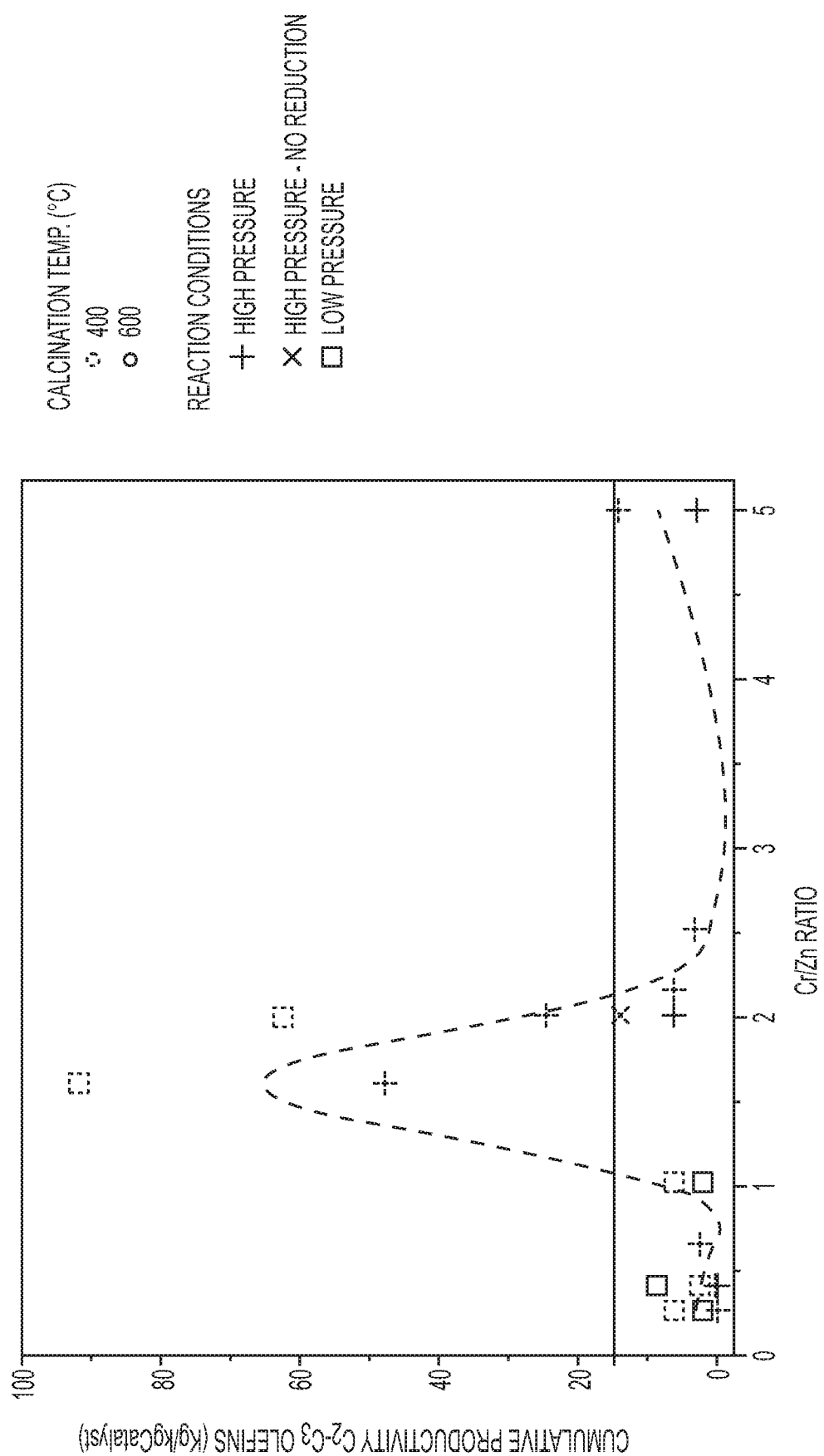

PROCESS TO CONVERT SYNTHESIS GAS TO OLEFINS USING A BIFUNCTIONAL CHROMIUM/ZINC OXIDE-SAPO-34 CATALYST

CROSS REFERENCE TO RELATED APPLICATION

This application claims priority to U.S. Provisional Patent Application Ser. No. 62/438,035 filed Dec. 22, 2016, which is incorporated by reference herein in its entirety.

TECHNICAL FIELD

The present disclosure relates to the field of producing olefins from a feed stream containing carbon. More particularly, the disclosure relates to producing a product mixture comprising $C_2$ and $C_3$ olefins from a feed stream containing hydrogen and carbon monoxide in the presence of a bifunctional catalyst.

BACKGROUND

For a number of industrial applications a desirable starting material is a lower olefin, particularly olefins comprising $C_2$, $C_3$, or a combination thereof that can then be converted to industrially desirable materials, such as for producing plastics, fuels, and various downstream chemicals. A variety of methods of producing these has been developed, including petroleum cracking of paraffins and various synthetic processes.

For example, some industrial processes for converting a synthesis gas (syngas) feed to olefins have been developed; among them is the well-known Fischer-Tropsch (FT) process where a mixture of olefins can be produced along with, primarily, longer chain paraffins. This broad product distribution is unfortunately typical for FT processes, and the selectivity to the desired lower olefins obtained via the syngas conversion is typically relatively limited. In response to this, some variations of the FT process have been developed to increase the selectivity to lower olefins.

Despite extensive research in this area, problems generally encountered have included unacceptable levels of co-products such as methanol, methane, $C_2$ and $C_3$ paraffins, and/or $C_{4+}$ products, which require expensive separation and recycling in order to effectively utilize the $C_2$ and $C_3$ olefins for their desired purpose(s). Thus, there remains a need in the art for processes that are effective to produce $C_2$ and $C_3$ olefins—and having reduced amounts of methanol, methane, $C_2+C_3$ paraffins, and/or $C_4$ and higher products—that still enable desired levels of feed stream conversion. It is also desirable that a variety of feed streams may be used and still result in the same or a very similar product distribution, which reduces requirements for feed stream purity and/or feed stream costs. It is also desirable that any catalyst(s) used has/have desirably long lifetimes under processing conditions. Finally, it is desirable that such process minimizes or does not involve production of an intermediate product stream of, for example, methanol, dimethyl ether (DME) or other oxygenates which would then need to be separately converted to the desired hydrocarbon product, i.e., a $C_2$ and/or $C_3$ olefin product.

SUMMARY

According to one embodiment, a process for preparing $C_2$ to $C_3$ olefins, comprises: introducing a feed stream into a reactor, wherein the feed stream comprises hydrogen gas and carbon monoxide gas, such that a volumetric ratio of hydrogen to carbon monoxide ranges from greater than 0.5:1 to less than 5:1; and contacting the feed stream with a bifunctional catalyst in the reactor. The bifunctional catalyst comprises: (1) Cr/Zn oxide methanol synthesis component having a Cr to Zn molar ratio from greater than 1.0:1 to less than 2.15:1, and (2) a SAPO-34 silicoaluminophosphate microporous crystalline material. The reactor operates at the following reaction conditions comprising: (a) a reactor temperature ranging from 350° C. to 450° C.; and (b) a pressure ranging from 10 bar (1.0 MPa) to 60 bar (6.0 MPa). The process has a cumulative productivity of $C_2$ to $C_3$ olefins greater than 15 kg $C_2$ to $C_3$ olefins/kg catalyst.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWING

The FIGURE is a plot of cumulative $C_2$-$C_3$ olefins productivity versus molar ratio of chromium to zinc in the Cr/Zn oxide catalyst of the bifunctional catalyst according to embodiments disclosed and described herein.

DETAILED DESCRIPTION

Reference will now be made in detail to embodiments of processes for converting synthesis gas to olefins using a bifunctional Cr/Zn oxide-SAPO-34 catalyst. In one embodiment, a process for preparing $C_2$ to $C_3$ olefins, comprising: introducing a feed stream into a reactor, wherein the feed stream comprises hydrogen gas and carbon monoxide gas, such that a volumetric ratio of hydrogen to carbon monoxide ranges from greater than 0.5:1 to less than 5:1; and contacting the feed stream with a bifunctional catalyst in the reactor, wherein the bifunctional catalyst comprises: (1) Cr/Zn oxide methanol synthesis component having a Cr to Zn molar ratio from greater than 1.0:1 to less than 2.15:1, and (2) a SAPO-34 silicoaluminophosphate microporous crystalline material. The reactor operates at the following reaction conditions comprising: (a) a reactor temperature ranging from 350° C. to 450° C.; and (b) a pressure ranging from 10 bar (1.0 MPa) to 60 bar (6.0 MPa). The process has a cumulative productivity of $C_2$ to $C_3$ olefins greater than 15 kg $C_2$ to $C_3$ olefins/kg catalyst. Various processes for converting synthesis gas to olefins using a bifunctional Cr/Zn oxide-SAPO-34 catalyst will be described herein. In embodiments, the weight ratio of the Cr/Zn oxide methanol synthesis component to the SAPO-34 silicoaluminophosphate microporous crystalline material is from 0.1:1 to 10:1.

In general, embodiments provide a relatively convenient and efficient means of preparing lower hydrocarbons, and in particular $C_2$-$C_3$ olefins, from a carbon-containing feed stream, such as, for example, a feed stream comprising hydrogen ($H_2$) and carbon monoxide (CO). In embodiments, a bifunctional catalyst is used, which targets the problem of broad product distribution encountered in certain processes, such as FT processes, that convert syngas using iron-containing or cobalt-containing catalysts. Such processes may produce a wide product distribution (frequently such product distributions comprise olefins, paraffins, and oxygenates with carbon numbers ranging from $C_1$ to $C_{20+}$), a comparatively lower yield of short chain olefins, and significant methane production.

Embodiments also successfully address one particular problem related to the methane to olefins (MTO) process, which is that catalysts used therein typically have relatively short lifetimes and therefore must be frequently regenerated. Processes according to embodiments, by comparison, offer a significantly greater catalyst lifetime, in some cases by a factor of more than 10, than many traditional MTO catalysts. For further discussion of MTO catalyst deactivation, see, e.g., X. Wu, et al., "Methanol conversion on SAPO-34: reaction condition for fixed bed reactor," *Appl. Catal. A: Gen.* 260, 63-69, 2004 and U.S. Pat. No. 7,166,757 B2.

Finally, processes according to embodiments are operable in a single unit, which may reduce or eliminate costs and the problems associated with multiple unit operations. One example of such a multiple unit operation for producing olefins are MTO processes, which require a two-step protocol wherein methanol is produced first, and then the methanol is used to make the lower olefins. This may be further complicated by addition of a third step, i.e., a (higher) olefins cracking process (OCP). In contrast, processes of embodiments are capable of producing comparable or higher amounts of the $C_2$ and $C_3$ olefins via a single step.

In some embodiments, an appropriate feed for conversion should be selected. The processes of embodiments has utility in that it converts a feed stream that comprises, consists essentially of, or consists of $H_2$ gas and CO gas, to a product mixture that comprises a combination of unsaturated two carbon atom and three carbon atom hydrocarbons, such as, for example, $C_2$ and $C_3$ olefins. The product mixture itself has utility as a starting material or intermediate to produce a range of chemical products including plastics, commodity chemicals, and the like. As will be recognized by those skilled in the art, there is often an additional component that may be present in the feed, including in particular a minor proportion of carbon dioxide ($CO_2$) (which is often, although not always, a component of syngas), inert gases, such as nitrogen ($N_2$), additional carbon-containing compounds, such as methane ($CH_4$), another hydrocarbon, such as a small amount of ethane ($C_2H_6$) or ethylene ($C_2H_4$), or combinations of the foregoing. The outlet stream, in embodiments, may contain CO, $CO_2$, water ($H_2O$), and $H_2$ originating from unconverted feed stream components, the Water Gas Shift reaction (which produces $CO_2$ and $H_2$), and/or the reverse of the Water Gas Shift reaction (which produces CO and $H_2O$). It should be understood that control of feed stream composition can be used to help tailor the final product toward the more desired products.

In some embodiments, CO is present in the feed stream in an amount of at least 50 mol %, such as at least 60 mol %, at least 70 mol %, at least 80 mol %, or at least 90 mol %, based on the total composition of the feed stream, excluding $H_2$ gas. Accordingly, in other embodiments, inert gases (such as nitrogen or noble gases), methane, other carbon-containing compounds (such as $CO_2$, methane, and other hydrocarbons), may be present in the feed stream, in total, in amounts less than or equal to 50 mol %, such as less than 40 mol %, less than 30 mol %, less than 20 mol %, or less than 10 mol %, based on total feed stream, excluding $H_2$ gas. The $H_2$ gas is separately measured and, in some embodiments, is present in the total feed stream in a volumetric ratio of $H_2$ to CO ($H_2$:CO) that is greater than 0.5:1, greater than 0.6:1, or greater than or equal to 1:1. In some embodiments, the amount volumetric ratio of $H_2$ is less than 5:1, less than 3:1, or less than 2:1.

Processes according to embodiments also employ a particular bifunctional catalyst that, in combination with certain process parameters and with a selected feed stream, produces a particularly desirable and surprising product mix, wherein the yield of target $C_2$ and $C_3$ products (such as $C_2$ to $C_3$ olefins) is increased, while the yield of $C_2$ and $C_3$ paraffins, $C_{4+}$ hydrocarbons, oxygenates, and methane products is reduced in comparison with some other $C_2$-$C_3$ olefin targeted processes. Furthermore, this bifunctional catalyst shows a relatively stable conversion over time.

In certain embodiments, the bifunctional catalyst includes two components. The first component is a mixed metal oxides component, which is alternatively termed a "syngas-to-methanol component," or "methanol synthesis component." This component of the bifunctional catalyst comprises, consists essentially of, or consists of both chromium oxide ($Cr_2O_3$) and zinc oxide (ZnO). Because of the nature of mixtures of oxides, this component will in many embodiments also include phases wherein an oxygen atom or an oxide moiety may be bound covalently to at least one chromium atom or chromium moiety and, at the same time, the oxygen atom or oxide moiety may be bound to at least one zinc atom or zinc moiety. These materials where the bonding is undetermined are referred to herein as "mixed phases". Accordingly, the term "Cr/Zn oxide", as used herein, includes materials having mixed phases as well as materials having distinct $Cr_2O_3$ and ZnO phases. Such phases may form and reform as the bifunctional catalyst is used in the processes according to embodiments.

The second component of the bifunctional catalyst according to embodiments is a microporous crystalline material having 8-member ring (MR) access as defined by the Structure Commission of the International Zeolite Association (IZA) as CHA. In some embodiments, the component is SAPO-34 molecular sieve. Because the ring structure of SAPO-34 is known, it is also known that its pore opening has a diameter of approximately 3.8 Angstroms (Å), i.e., 0.38 nanometers (nm). This SAPO-34 molecular sieve is a silicoaluminophosphate material having a silicon content of at least 0.01 wt %, such as at least 0.1 wt %, or at least 0.5 wt %, based on total weight of the SAPO-34. Other than the substitution of the silicon in the crystal lattice that would otherwise be an aluminophosphate lattice, the SAPO-34 used in some embodiments does not include any other metal atoms, i.e., heteroatoms, in significant amounts, although trace amounts of other metals may result from the preparation process, but these amounts of metals is not sufficient to significantly alter the efficacy and overall effect of the SAPO-34 in processes according to embodiments. As the term is used herein, "trace amounts" represent amounts less than 1.0 wt %, such as less than 0.5 wt %, less than 0.1 wt %, or less than 0.005 wt %. Accordingly, it will be understood by those skilled in the art that the elemental framework composition of the anhydrous form of SAPO-34 may be represented as $(Si_xAl_yP_z)O_2$, where x, y and z represent molar fractions of silicon, aluminum and phosphorus, with x+y+z=1. See, for example, Lok, B. M., et al., "Silicoalumino-phosphate Molecular Sieves: Another New Class of Microporous Crystalline Inorganic Solids," *J. Am. Chem. Soc.* 106 (1984) 6092-6093.

Notwithstanding the above, the SAPO-34 may be used in its acid form. Those skilled in the art will understand that in its acid form the cations charge balancing the framework consists predominantly of proton ions $H^+$. In other embodiments some fraction of the $H^+$ ions can be substituted with other ions, for example, those of the alkaline or alkali group of metals, or other metals such as, for example, chromium or zinc from the methanol synthesis component.

It should be noted that using SAPO-34 as the microporous crystalline material allows for improved conversion selectivity of $C_2$-$C_3$ olefins as compared to other known microporous crystalline materials. As an example, while ZSM-5 has been studied extensively for use as a microporous crystalline materials in various conversion reactions, when ZSM-5 is used in combination with the methanol synthesis component disclosed and described herein, the resultant product stream is high in hydrocarbons but does not yield the same concentration of $C_2$-$C_3$ olefins that is realized when SAPO-34 is used as the microporous crystalline material.

According to some embodiments, preparing the methanol synthesis components includes separately preparing the two oxides ($Cr_2O_3$ and ZnO) and then combining the prepared oxides. In other embodiments, the two oxides ($Cr_2O_3$ and ZnO) may be made at the same time in a single reaction process. Methods for preparing the two oxides of the methanol synthesis component are understood by those skilled in the art. In one or more embodiments, the chromium content in the methanol synthesis component independently ranges from 33 wt % to 46 wt %, such as from 41 wt % to 45 wt %, and the zinc content independently ranges from 27 wt % to 42 wt %, such as from 28 wt % to 32 wt %. Each of the weight percents is based upon the combined weight percents of all metals in the mixed metal oxides. The oxygen, in the form of an oxide moiety, in each catalyst is therefore present in an amount determined by subtracting the sum of the weight percent of each of the component metals from 100 wt %.

Notwithstanding the above, in embodiments, the constituents of the mixed metal oxides component be consistently measured in terms of atomic, i.e., molar, ratios, to avoid small inconsistencies that may arise when both weight percent ratios and molar ratios are employed and/or when rounding is carried out in a conversion. For example, in embodiments the chromium and zinc contents in the mixed metal oxides component are such that the atomic (molar) ratio of chromium to zinc ranges from greater than 1.0:1 to less than 2.15:1, such as from 1.1:1 to less than 2.15:1, from 1.2:1 to less than 2.15:1, from 1.3:1 to less than 2.15:1, from 1.4:1 to less than 2.15:1, from 1.5:1 to less than 2.15:1, from 1.6:1 to less than 2.15:1, from 1.7:1 to less than 2.15:1, from 1.8:1 to less than 2.15:1, from 1.9:1 to less than 2.15:1, or from 2.0:1 to less than 2.15:1. In other embodiments, the molar ratio of chromium to zinc is from greater than 1.0:1 to 2.1:1, such as from greater than 1.0:1 to 2.0:1, from greater than 1.0:1 to 1.9:1, from greater than 1.0:1 to 1.8:1, from greater than 1.0:1 to 1.7:1, from greater than 1.0:1 to 1.6:1, from greater than 1.0:1 to 1.5:1 from greater than 1.0:1 to 1.4:1, from greater than 1.0:1 to 1.3:1, from greater than 1.0:1 to 1.2:1, or from greater than 1.0:1 to 1.1:1. In still other embodiments, the molar ratio of chromium to zinc is from 1.1:1 to 2.0:1, such as from 1.2:1 to 1.9:1, from 1.3:1 to 1.8:1, from 1.4:1 to 1.7:1, or from 1.5:1 to 1.6:1. In still other embodiments, the molar ratio of chromium to zinc is from 1.4:1 to 2.1:1, such as from 1.6:1 to 2.0:1.

In further embodiments, the methanol synthesis component, once formulated, may be calcined to form a mixed metal oxide that can be used in the bifunctional catalyst. The calcination temperature in some embodiments may be from 350° C. to 600° C., from 375° C. to 575° C., from 400° C. to 550° C., from 425° C. to 525° C., or from 450° C. to 500° C. In a particular embodiment, the calcination temperature of the mixed metal oxide is 375° C. to 425° C., for example about 400° C. As is apparent to one of ordinary skill in the art, if the calcination temperature is too low, the mixed metal oxide will not be calcined. However, when the calcination temperature is too high, such as, for example, at or above 600° C., the performance of the mixed metal oxide to produce $C_2$-$C_3$ olefins decreases. Without being bound by any particular theory, it is believed that calcining at temperature at or above 600° C. segregates the ZnO phase from the Cr/Zn mixed phase, thereby increasing the hydrogenation capability of the mixed metal oxide.

In another (non-ordered) step, the SAPO-34 component may be prepared, prior to combining it with the methanol synthesis component, via a templating method that is well-known to those skilled in the art. See, e.g., U.S. Patent Application Publication 2015/0232345; G. Liu, et al., "Synthesis of SAPO-34 templated by diethylamine: Crystallization process and Si distribution in the crystals," *Microporous and Mesoporous Materials,* 114 (2008) 1-3, 416-423; Online publication of International Zeolite Association www.iza-online.org/synthesis/Recipes/SAPO-34.html (includes XRD pattern); and/or L. P. Ye, et al., "Synthesis Optimization of SAPO-34 in the Presence of Mixed Template for MTO Process," *Adv. Matl. Research,* 132 (2010) 246-256.

As it is known to those skilled in the art, after preparation and before use, SAPO-34 may be calcined to remove at least a portion of the templating agent. See, for example, U.S. Pat. No. 4,440,871. The calcination may be accomplished by placing SAPO-34 in an oxygen-containing gas stream, such as, for example, air and gradually increasing the temperature to a temperature effective for removing at least a portion of the templating agent. Generally, this temperature is between 200° C. and 700° C., such as, for example, 600° C. The SAPO-34 may then be held at that temperature for a time period sufficient to remove the templating agent, such as, for example, from 1 to 24 hours. In some embodiments, the SAPO-34 may be held at this temperature for about 4 hours.

Once the two components have been prepared, they may be mixed together using any means and methods generally known to those skilled in the art to maximize distribution of the components within the bifunctional catalyst, thereby theoretically optimizing their joint effect on any given volume of feed stream. In embodiments the components are combined in proportion such that, in the reactor bed (whether fixed, moving and/or fluidized), they will be in a weight/weight (wt/wt) ratio of mixed metal oxides component:SAPO-34 component ranging from 0.1:1 to 10:1, such as from 0.5:1 to 8:1, or from 1:1 to 5:1.

In one or more process embodiments, a feed stream is passed into a reactor via a heated reactor inlet. In the reactor, the feed stream moves over and/or through the catalyst bed which has been appropriately loaded with the bifunctional catalyst according to embodiments. Reaction conditions should be sufficient to convert at least a portion of the carbon-containing gas, i.e., particularly the predominant CO gas, into a product mixture, which will be described hereinbelow. The conditions under which this process may be carried out comprise, consist essentially of, or consist of: (1) a reactor temperature ranging from 350° C. to 450° C.; and (2) a pressure ranging from 10 bar (1.0 MPa) to 60 bar (6.0

MPa). In some embodiments it is also desirable, for reasons of acceptable industrial productivity, for the feed stream's gas hourly space velocity (GHSV) to be greater than 500 reciprocal hours ($h^{-1}$).

In particular embodiments, the bifunctional catalyst may be reduced prior to passing a feed stream into the reactor. Reduction procedures are known to those of ordinary skill in the art and generally involve contacting the catalyst with gas stream comprising hydrogen to at least partially reduce the metal oxides present in the catalyst. The conditions for the reduction process may, in embodiments, include a pressure from ambient to process pressure, and a temperature from 200° C. to 500° C., such as, for example, from 350° C. to 450° C. or even about 400° C. The duration of the reduction process may, in some embodiments, be from 1 hr to 24 hrs, such as, for example, about 2 hours.

As used hereinabove, the phrase "reactor temperature" will be understood to represent either an average reactor temperature, where temperature is measured at more than one location within the reactor, or the sole temperature, where temperature is measured at only one location within the reactor. However, those skilled in the art will recognize that the temperature at different locations within the reactor will almost certainly vary somewhat, according to feed stream component flow rates, catalyst flow where moving/fluidized bed reactors are employed, bed packing, reactor size and geometry, variations in reactor inlet temperatures, and so forth, and will be able to easily adjust process parameters and other means to control "reactor temperature," to ensure that the reactor temperature requirements of embodiments are met. In addition to making modifications of the reaction parameters listed hereinabove, those skilled in the art may also design a given system such that additional and/or alternative means of temperature control, such as the use of a multi-tube heat exchanger, may be employed.

In certain embodiments, such reaction conditions comprise, consist essentially of, or consist of: (1) a reactor temperature ranging from greater than 350° C., such as greater than 360° C., greater than 380° C., or greater than 390° C. to less than 450° C., such as less than 430° C., less than 420° C., or less than 410° C.; (2) a pressure ranging from greater than 10 bar (1.0 MPa), greater than 15 bar (1.5 MPa), or greater than 20 bar (2.0 MPa), to less than 60 bar (6.0 MPa), such as less than 55 bar (5.5 MPa), or less than 50 bar (5.0 MPa); and (3) a GHSV of greater than 500 $h^{-1}$, such as greater than 800 $h^{-1}$, or greater than 1,000 $h^{-1}$, to less than 12,000 $h^{-1}$, such as less than 10,000 $h^{-1}$, or less than 8,000 $h^{-1}$.

As noted above, embodiments of processes for converting a feed stream to olefins may be conducted at relatively high pressures compared to conventional processes for converting a feed stream to olefins. Many conventional methods process feed streams at pressures less than about 5 bar (0.5 MPa). In contrast, the bifunctional catalyst disclosed herein allows for conversion of a feed stream to $C_2$-$C_3$ olefins at much higher pressures (such as greater than 10 bar (1 MPa), greater than 30 bar (3 MPa), greater than 45 bar (4.5 MPa). In some embodiments, the pressure may be from 20 bar (2.0 MPa) to 50 bar (5.0 MPa)), such as from 25 bar (2.5 MPa) to 45 bar (4.5 MPa). This increased pressure helps maintain the stability of the bifunctional catalyst for long periods of time. However, even at the high pressures used in some embodiments, olefin selectivity in the product stream (i.e., the ability of the bifunctional catalyst to produce $C_2$-$C_3$ olefins) is acceptable. In addition, the high operating pressure increases the feed conversion, which in turn improves the catalyst productivity.

The outlet stream will, as will be understood by the skilled artist, contain proportions of the product mixture and the unconverted feed stream gases, as well as, typically, a significant amount of water resulting from the reactions which take place. The amount of each will vary according to a variety of factors well known to those skilled in the art, including carbon conversion, yield, catalyst productivity, time on stream, and so forth. The unconverted feed stream gases may be separated from the product mixture and, if desired, recycled back into the process again as a portion of the feed stream. Alternatively, such may be disposed of in an environmentally approved and responsible manner, as will be well-known to those skilled in the art.

One way to measure the effectiveness of the processes according to embodiments is by measuring the cumulative productivity of $C_2$ to $C_3$ olefins per catalyst expended. The cumulative productivity of $C_2$ to $C_3$ olefins per catalyst expended is calculated by plotting the yield of $C_2$ to $C_3$ olefins vs. cumulative productivity of $C_2$ to $C_3$ olefins (kg $C_2$ to $C_3$ olefins/kg catalyst) and then extrapolating to the point where the yield to $C_2$ to $C_3$ olefins has dropped to zero. In some embodiments, the cumulative productivity of $C_2$ to $C_3$ olefins per catalyst expended is greater than 15 kg $C_2$ to $C_3$ olefins/kg catalyst, greater than 20 kg $C_2$ to $C_3$ olefins/kg catalyst, greater than 25 kg $C_2$ to $C_3$ olefins/kg catalyst, greater than 30 kg $C_2$ to $C_3$ olefins/kg catalyst, or greater than 35 kg $C_2$ to $C_3$ olefins/kg catalyst. In other embodiments, the cumulative productivity of $C_2$ to $C_3$ olefins per catalyst expended is from 15 kg $C_2$ to $C_3$ olefins/kg catalyst to 90 kg $C_2$ to $C_3$ olefins/kg catalyst, such as 20 kg $C_2$ to $C_3$ olefins/kg catalyst to 85 kg $C_2$ to $C_3$ olefins/kg catalyst, 25 kg $C_2$ to $C_3$ olefins/kg catalyst to 80 kg $C_2$ to $C_3$ olefins/kg catalyst, 30 kg $C_2$ to $C_3$ olefins/kg catalyst to 75 kg $C_2$ to $C_3$ olefins/kg catalyst, 35 kg $C_2$ to $C_3$ olefins/kg catalyst to 70 kg $C_2$ to $C_3$ olefins/kg catalyst, 40 kg $C_2$ to $C_3$ olefins/kg catalyst to 65 kg $C_2$ to $C_3$ olefins/kg catalyst, 45 kg $C_2$ to $C_3$ olefins/kg catalyst to 60 kg $C_2$ to $C_3$ olefins/kg catalyst, or 50 kg $C_2$ to $C_3$ olefins/kg catalyst to 55 kg $C_2$ to $C_3$ olefins/kg catalyst. In yet other embodiments, the cumulative productivity of $C_2$ to $C_3$ olefins per catalyst expended is 35 kg $C_2$ to $C_3$ olefins/kg catalyst to 75 kg $C_2$ to $C_3$ olefins/kg catalyst, such as 40 kg $C_2$ to $C_3$ olefins/kg catalyst to 70 kg $C_2$ to $C_3$ olefins/kg catalyst, or 45 kg $C_2$ to $C_3$ olefins/kg catalyst to 65 kg $C_2$ to $C_3$ olefins/kg catalyst.

Examples

Embodiments will be further clarified by the following example.

Initially, SAPO-34 was formed by stirring together 8.2 grams of aluminum isopropoxide ($Al(OC_3H_7)_3$) with a solution of 3.9 grams of 85 wt % orthophosphoric acid in 8.4 grams of water. Subsequently, 1.2 grams of an aqueous sol of 30 wt % $SiO_2$ (Ludox AS-30) and 0.5 grams of water were stirred into the mixture until the resultant was homogeneous. Finally, 16.8 grams of an aqueous solution of 35 wt % tetraethylammonium hydroxide (TEAOH) was added to the mixture to form the reaction mixture.

Once formulated, the reaction mixture was placed in a stainless steel stirred Parr reactor and heated to 200° C. at 0.5° C./min. The temperature was maintained for 120 hours under autogenous pressure while stirring at 60 RPM. The product was recovered by centrifugation, washed with water and dried at 90° C. overnight.

A portion of the recovered product required for catalytic testing was calcined in a muffle furnace in air to remove the templating agent. This was accomplished by gradually increasing the temperature in the furnace to 600° C. at a heating rate of 2° C./min, and holding at 600° C. for a period of 4 hours. This calcined material was used in the subsequent examples and comparative examples as the SAPO-34 component.

The Cr/Zn oxide was formulated as follows: Appropriate quantities of $Cr(NO_3)_3 \cdot 9H_2O$ and $Zn(NO_3)_2 \cdot 3H_2O$ were added to distilled water ($H_2O$). In addition, a 0.5 M solution of $(NH_4)_2CO_3$ was prepared as a precipitating agent. The cation ($Cr^{3+}/Zn^{2+}$) and anion (($CO_3)^{2-}$) solutions were simultaneously added drop-wise to a stirred beaker of distilled $H_2O$ and maintained at $7.0 \leq pH \leq 7.5$ and T=338±5 K. Co-precipitated materials were filtered, washed with distilled water, dried in static air at 383 K, and subsequently calcined at 673 K or 873 K for 2 h.

Prior to catalytic testing, 1 gram of Cr/Zn oxide catalyst was physically mixed with 0.5 gram of SAPO-34 by shaking them together in a bottle. Each of the catalysts has a particle size before mixing within a range of from 40 mesh (0.422 millimeter) to 80 mesh (0.178 millimeter).

Table 1 below provides the Cr/Zn molar ratio for each of the examples and comparative examples, as well as the calcination temperature for the Cr/Zn oxide.

TABLE 1

| Example | Cr/Zn molar ratio | Calcination Temperature (° C.) | Process Conditions | Cum. Productivity (kg $C_2$-$C_3$ Olefins/ kg catalyst) |
|---|---|---|---|---|
| Ex. 1 | 1.60 | 400 | High P | 48.2 |
| Ex. 2 | 1.60 | 400 | Low P | 92.3 |
| Ex. 3 | 2.00 | 400 | High P | 25.1 |
| Ex. 4 | 2.00 | 400 | Low P | 62.8 |
| Comp. Ex. 1 | 2.00 | 400 | High P -no reduction | 14.4 |
| Comp. Ex. 2 | 0.25 | 400 | High P | 0.2 |
| Comp. Ex. 3 | 0.25 | 400 | Low P | 6.5 |
| Comp. Ex. 4 | 0.25 | 600 | Low P | 2.4 |
| Comp. Ex. 5 | 0.40 | 600 | Low P | 9.1 |
| Comp. Ex. 6 | 0.40 | 400 | High P | 1.0 |
| Comp. Ex. 7 | 0.40 | 400 | Low P | 2.6 |
| Comp. Ex. 8 | 0.40 | 600 | High P | 0.4 |
| Comp. Ex. 9 | 0.65 | 400 | High P | 2.7 |
| Comp. Ex. 10 | 1.00 | 400 | Low P | 6.5 |
| Comp. Ex. 11 | 1.00 | 600 | Low P | 2.3 |
| Comp. Ex. 12 | 2.00 | 600 | High P | 6.6 |
| Comp. Ex. 13 | 2.15 | 400 | High P | 6.8 |
| Comp. Ex. 14 | 2.50 | 400 | High P | 3.4 |
| Comp. Ex. 15 | 5.00 | 400 | High P | 14.5 |
| Comp. Ex. 16 | 5.00 | 600 | High P | 3.4 |

In Table 1, "High P" indicates that the catalyst was reduced under a stream composed of 22.5 ml/min $H_2$ and 11.25 ml/min $N_2$ for 2 hours at 400° C. The system was then purged with pure nitrogen while keeping the temperature at 400° C. The system was then pressurized with pure nitrogen up to 50 bar (5.0 MPa), and 22.5 ml/min CO, 67.5 ml/min $H_2$, and 10 ml/min He was passed over the catalyst (WHSV=1.4 $hr^{-1}$).

In Table 1, "Low P" indicates that the system was pressurized with pure nitrogen up to 20 bar (2.0 MPa) and then heated up to 400° C. while still flowing pure nitrogen. Subsequently 15 ml/min CO, 30 ml/min $H_2$, and 5 ml/min He was passed over the catalyst. (WHSV=0.9 $hr^{-1}$).

The catalytic performance of the Cr/Zn oxide-SAPO-34 hybrid bifunctional catalyst is expressed as cumulative productivity of $C_2$ to $C_3$ olefins (kg $C_2$ to $C_3$ olefins/kg catalyst). This value is calculated by plotting the yield of $C_2$ to $C_3$ olefins vs. cumulative productivity of $C_2$ to $C_3$ olefins (kg $C_2$ to $C_3$ olefins/kg catalyst) and then extrapolating to the point where the yield to $C_2$ to $C_3$ olefins has dropped to zero. The results are provided in Table 1 above and shown in the FIGURE.

The examples and comparative examples showed that a Cr/Zn molar ratio higher than 1:1 and lower than 2.15:1 obtained a high productivity of $C_2$ to $C_3$ olefins in syngas-to-olefins process (See Examples 1-4). At "High P" process conditions (50 bar, $H_2$/CO 3:1, with pre-reduction of the catalyst prior to contacting with syngas), catalysts prepared with this specific Cr/Zn molar ratio (1<x<2.15) showed higher olefin productivity (Examples 1 and 3). In this specific Cr/Zn range operating at "Low P" process conditions resulted in even higher productivity to $C_2$ to $C_3$ olefins when compared to operating at "High P" process conditions (Examples 2 and 4). Furthermore, calcining the Cr/Zn oxide catalyst at 400° C. (Example 3) led to better catalytic performance than calcining this catalyst at 600° C. (Comparative Example 12). The Cr/Zn oxide catalyst prepared with a Cr/Zn molar ratio of 2 and calcined at 400° C. shows lower catalytic performance when tested at "High P" process conditions without the reduction step (Comparative Example 1). However, the performance of this catalyst is the highest when tested at "Low P" process conditions (thus, no reduction) (Example 4). Hence, the desire for reducing the catalyst prior to contacting with syngas might depend on the process conditions.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A process for preparing $C_2$ to $C_3$ olefins, comprising:
   introducing a feed stream into a reactor, wherein the feed stream comprises hydrogen gas and carbon monoxide gas, such that a volumetric ratio of hydrogen to carbon monoxide ranges from greater than 0.5:1 to less than 5:1; and
   contacting the feed stream with a bifunctional catalyst in the reactor, wherein the bifunctional catalyst comprises: (1) Cr/Zn oxide methanol synthesis component having a Cr to Zn molar ratio from greater than 1.0:1 to less than 2.15:1, and (2) a SAPO-34 silicoaluminophosphate microporous crystalline material,
   wherein the reactor operates at reaction conditions comprising:
   (a) a reactor temperature ranging from 350° C. to 450° C.; and
   (b) a pressure ranging from 10 bar (1.0 MPa) to 60 bar (6.0 MPa), and
   wherein the process has a cumulative productivity of $C_2$ to $C_3$ olefins greater than 15 kg $C_2$ to $C_3$ olefins/kg catalyst.

2. The process for preparing $C_2$ to $C_3$ olefins according to claim 1, wherein the Cr to Zn molar ratio is at least 1.1:1 and less than 2.15:1.

3. The process for preparing $C_2$ to $C_3$ olefins according to claim 1, wherein the Cr to Zn molar ratio is at least 1.5:1 and less than 2.15:1.

4. The process for preparing $C_2$ to $C_3$ olefins according to claim 1, wherein the reaction conditions comprises a pressure ranging from greater than 30 bar (3.0 MPa) to 60 bar (6.0 MPa).

5. The process for preparing $C_2$ to $C_3$ olefins according to claim 1, wherein the reaction conditions comprises a pressure ranging from greater than 45 bar (4.5 MPa) to 60 bar (6.0 MPa).

6. The process for preparing $C_2$ to $C_3$ olefins according to claim 1, wherein the methanol synthesis component is calcined at a temperature from 350° C. to 600° C.

7. The process for preparing $C_2$ to $C_3$ olefins according to claim 1, wherein the methanol synthesis component is calcined at a temperature from 375° C. to 425° C.

8. The process for preparing $C_2$ to $C_3$ olefins according to claim 1, further comprising as a reaction condition a gas hourly space velocity of from 500 reciprocal hours to 12,000 reciprocal hours.

9. The process for preparing $C_2$ to $C_3$ olefins according to claim 1, wherein the volumetric ratio of hydrogen to carbon monoxide in the feed stream is from 0.5:1 to 3:1.

10. The process for preparing $C_2$ to $C_3$ olefins according to claim 1, wherein a weight ratio of the Cr/Zn oxide methanol synthesis component to the SAPO-34 silicoaluminophosphate microporous crystalline material is from 0.1:1 to 10:1.

11. The process for preparing $C_2$ to $C_3$ olefins according to claim 1, wherein the cumulative productivity of $C_2$ to $C_3$ olefins is from greater than 15 kg $C_2$ to $C_3$ olefins/kg catalyst to 90 kg $C_2$ to $C_3$ olefins/kg catalyst.

12. The process for preparing $C_2$ to $C_3$ olefins according to claim 1, wherein the bifunctional catalyst is reduced before the feed stream is contacted with the bifunctional catalyst.

13. The process for preparing $C_2$ to $C_3$ olefins according to claim 12, wherein the reaction conditions comprises a pressure ranging from greater than 50 bar (5.0 MPa) to 60 bar (6.0 MPa).

14. The process for preparing $C_2$ to $C_3$ olefins according to claim 3, wherein the reaction conditions comprises a pressure ranging from greater than 30 bar (3.0 MPa) to 60 bar (6.0 MPa).

15. The process for preparing $C_2$ to $C_3$ olefins according to claim 3, wherein the methanol synthesis component is calcined at a temperature from 375° C. to 425° C.

16. The process for preparing $C_2$ to $C_3$ olefins according to claim 3, further comprising as a reaction condition a gas hourly space velocity of from 500 reciprocal hours to 12,000 reciprocal hours.

17. The process for preparing $C_2$ to $C_3$ olefins according to claim 3, wherein a weight ratio of the Cr/Zn oxide methanol synthesis component to the SAPO-34 silicoaluminophosphate microporous crystalline material is from 0.1:1 to 10:1.

18. The process for preparing $C_2$ to $C_3$ olefins according to claim 3, wherein the bifunctional catalyst is reduced before the feed stream is contacted with the bifunctional catalyst.

19. A process for preparing $C_2$ to $C_3$ olefins, comprising:
   introducing a feed stream into a reactor, wherein the feed stream comprises hydrogen gas and carbon monoxide gas, such that a volumetric ratio of hydrogen to carbon monoxide ranges from greater than 0.5:1 to less than 3:1; and
   contacting the feed stream with a bifunctional catalyst in the reactor, wherein the bifunctional catalyst comprises: (1) Cr/Zn oxide methanol synthesis component having a Cr to Zn molar ratio from greater than 1.5:1 to less than 2.15:1, and (2) a SAPO-34 silicoaluminophosphate microporous crystalline material,
   wherein the reactor operates at reaction conditions comprising:
   (a) a reactor temperature ranging from 375° C. to 425° C.; and
   (b) a pressure ranging from 30 bar (3.0 MPa) to 60 bar (6.0 MPa), and wherein the process has a cumulative productivity of $C_2$ to $C_3$ olefins from greater than 15 kg $C_2$ to $C_3$ olefins/kg catalyst to 90 kg $C_2$ to $C_3$ olefins/kg catalyst.

20. The process for preparing $C_2$ to $C_3$ olefins according to claim 19, wherein the bifunctional catalyst is reduced before the feed stream is contacted with the bifunctional catalyst.

* * * * *